United States Patent [19]

Ison

[11] Patent Number: Plant 5,823

[45] Date of Patent: Dec. 9, 1986

[54] GRANNY VAL GRAPEVINE

[76] Inventor: Bill Ison, Rte. 1, Brooks, Ga. 30205

[21] Appl. No.: 670,052

[22] Filed: Nov. 9, 1984

[51] Int. Cl.[4] ..... A01H 5/03

[52] U.S. Cl. ..... Plt./47

[58] Field of Search ..... Plt./47

*Primary Examiner*—Robert E. Bagwill

*Attorney, Agent, or Firm*—Eugene T. Holmes

[57] ABSTRACT

A cross between the female variety Fry and the pollen parent variety Carlos, to produce an improved variety of self-fertile muscadine grape.

1 Drawing Figure

DESCRIPTION OF THE VARIETY

The primary objective of the breeding was to produce an improved variety of muscadine grape. The fruit of the new variety is large and bronze and has a dry stem scar. Other fruit characteristics of the new variety include even ripening, high sugar content and long shelf life. The new variety is self-fertile, as well as productive and vigorous.

In comparison with both seed and parent plant, the new variety is similar in size to the seed plant, also resembles the seed parent. The fruit of this new variety contains on the average 21.50 to 22.50 percent soluble solids, which is a higher sugar content than the fruit of both parents; also similar in color to the seed parent.

The present variety yields on the average of from 5 to 8 tons per acre in tests conducted at Ison's Nursery & Vineyards, Brooks, Ga. This variety is outstanding for fresh fruit, having excellent flavor.

Asexual reproduction of the new variety either by soft wood cuttings or by layering as performed at Brooks, Ga. show that the above characteristics and distinctions are true to form and are established and transmitted through succeeding propagations.

The accompanying photograph shows a typical specimen of the vegetative growth and fruit of the new variety when the fruit is ripe and ready for picking. The color is as nearly true as reasonably possible to make the same in color illustration of the characteristics.

The following is a detailed description of the new variety:

Species: *Vitis rotundifolia.*
Type: Vine.
Seed parent: Variety Fry.
Pollen parent: Variety Carlos.
Propagation: Holds its characteristics through succeeding propagation by either layering or by soft wood cuttings.
Locality where grown: Brooks, Ga.

Fruit borne: Usually in clusters of 14 to 18 berries.
Fruit size: Large, similar to seed parent, about $1\frac{1}{8}''$ diameter.
Fruit color: Greyed yellow Group 161A Fan 4 of The Royal Horticultural Society, London, England.
Sugar content: 21.50 to 22.50 percent soluble solids.
Fruit shape: Round.
Maturity date: Usually ripens about September 25, at Brooks, Ga.
Seed:
*Average diameter.*—$\frac{1}{8}''$.
*average seed per berry.*—2.65.
Pulp:
*Color group.*—Fan 4 195B The Royal Horticultural Society, London, England.
*Consistency.*—Medium soft when compared to most muscadine varieties.
Skin: Medium thick.
Foliage:
*Leaf color.*—Fan 3 137A of The Royal Horticultural Society, London, England.
*Size and shape.*—Similar to most varieties.
Productive organs: Self-fertile.
Flowers: Perfect.
Canes: Medium to large calipers.
Diseases: Tolerant of Black Rot and Ripe Rot.
Growth habits: Vine vigorous and productive, requires support.

This description was made from a muscadine vine grown at Ison's Nursery & Vineyards, Brooks, Ga.

DESCRIPTION OF THE DRAWING

There is attached hereto a permanently mounted color photograph accurately depicting the new plant and particularly the fruit and foliage thereof.

I claim:

1. The new and distinct variety of the specified plant as described and illustrated.

* * * * *

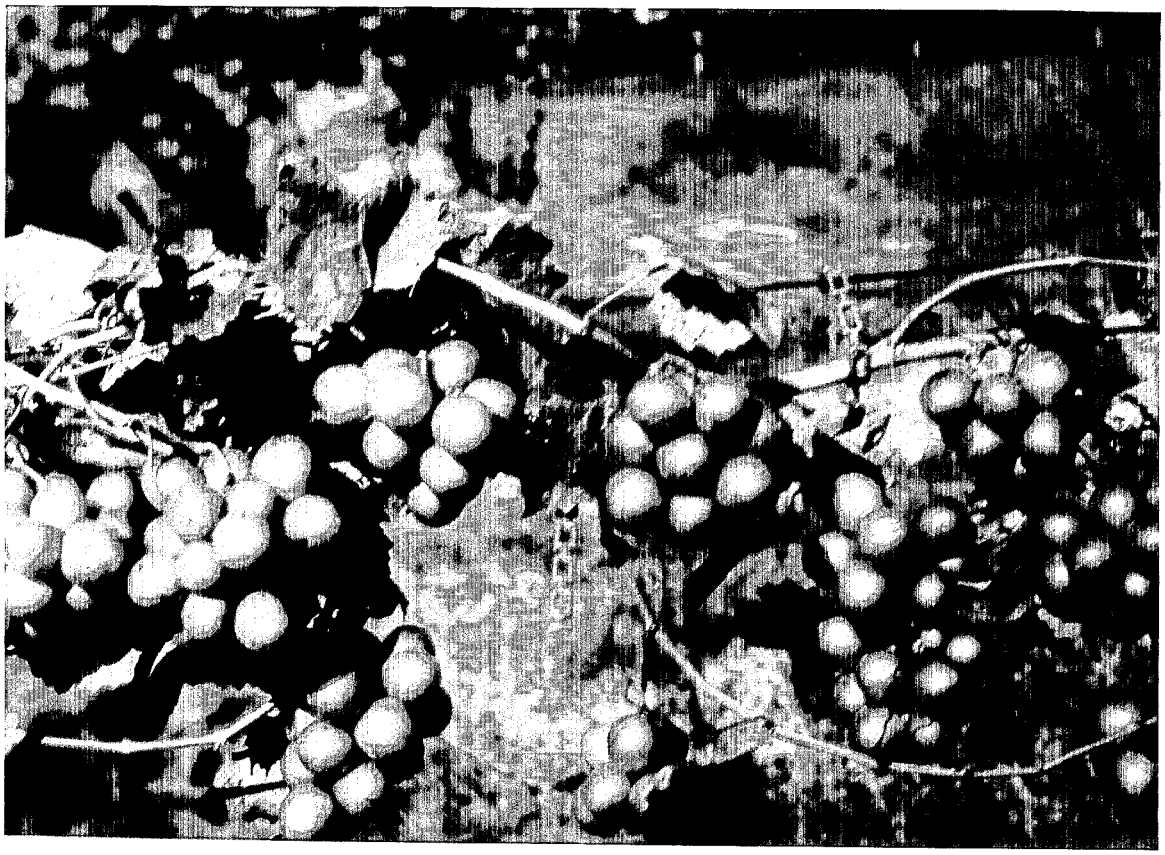

VARIETY "GRANNY VAL"